US009849202B2

(12) United States Patent
Jacob et al.

(10) Patent No.: US 9,849,202 B2
(45) Date of Patent: Dec. 26, 2017

(54) PLASMA POUCH

(75) Inventors: Jamey D. Jacob, Stillwater, OK (US); Kedar K. Pai, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 645 days.

(21) Appl. No.: 13/619,019

(22) Filed: Sep. 14, 2012

(65) Prior Publication Data

US 2014/0076712 A1 Mar. 20, 2014

(51) Int. Cl.
*A61L 2/14* (2006.01)
*H05H 1/24* (2006.01)

(52) U.S. Cl.
CPC ............ *A61L 2/14* (2013.01); *H05H 1/2406* (2013.01); *H05H 2001/2412* (2013.01); *H05H 2001/2418* (2013.01); *H05H 2001/2425* (2013.01); *Y10T 29/49147* (2015.01)

(58) Field of Classification Search
CPC ......... B01J 12/002; B01J 19/088; A61L 2/14; H05H 1/2406; H05H 2001/2425; H05H 2001/2412; H05H 2001/2418; Y10T 29/49147; B65B 55/12; H01J 37/32394; H01J 37/32568; H01J 37/32908; H01J 37/32798; C02F 1/78; A23L 3/34095
USPC ....... 422/186.04, 186.21–186.23, 1–43, 186, 422/22–24; 204/158.2
See application file for complete search history.

(56) References Cited

U.S. PATENT DOCUMENTS

| | | | |
|---|---|---|---|
| 6,446,887 B1 | 9/2002 | Swisher, Jr. et al. | |
| 7,504,066 B2 * | 3/2009 | Perlov et al. | 422/186.23 |
| 7,536,975 B2 * | 5/2009 | Denes et al. | 119/14.47 |
| 8,222,622 B2 * | 7/2012 | Hirasawa et al. | 250/492.3 |
| 2003/0180421 A1 * | 9/2003 | Ruan et al. | 426/237 |
| 2006/0244386 A1 | 11/2006 | Hooke et al. | |
| 2006/0251550 A1 | 11/2006 | Keras | |
| 2007/0089795 A1 | 4/2007 | Jacob | |
| 2008/0260578 A1 * | 10/2008 | Engemann et al. | 422/186.04 |
| 2010/0133386 A1 | 6/2010 | Schwimley et al. | |
| 2010/0175987 A1 * | 7/2010 | Creyghton et al. | 422/186.29 |
| 2010/0196626 A1 * | 8/2010 | Choi et al. | 427/569 |
| 2010/0209292 A1 * | 8/2010 | Hayashi et al. | 422/186.04 |
| 2010/0239466 A1 | 9/2010 | Rousseau et al. | |
| 2011/0022043 A1 * | 1/2011 | Wandke et al. | 422/28 |

(Continued)

FOREIGN PATENT DOCUMENTS

DE 102008045507 A1 * 4/2009 ............... A23L 3/26
JP 2008183025 A * 8/2008

(Continued)

OTHER PUBLICATIONS

Machine translation of JP 2008-183025A.*

(Continued)

*Primary Examiner* — Keith Hendricks
*Assistant Examiner* — Colleen M Raphael
(74) *Attorney, Agent, or Firm* — Crowe & Dunlevy; Terry L. Watt

(57) ABSTRACT

A device with a pouch having a pouch wall with an inner side and an outer side, the pouch wall defining an interior of the pouch. A plurality of electrodes embedded in the pouch wall with at least one electrode partially exposed within the interior of the pouch. The plurality of electrodes generate plasma within the interior of the pouch in response to application of an voltage to the plurality of electrodes.

12 Claims, 11 Drawing Sheets

(56) References Cited

U.S. PATENT DOCUMENTS

| | | | |
|---|---|---|---|
| 2011/0180149 A1 | 7/2011 | Fine et al. | |
| 2012/0070338 A1* | 3/2012 | Schaeffer | A61L 2/035 422/22 |
| 2012/0074830 A1* | 3/2012 | Eden et al. | 313/267 |
| 2012/0183437 A1* | 7/2012 | Keener | H05H 1/2406 422/23 |
| 2012/0288405 A1* | 11/2012 | Snowball | A61L 2/26 422/22 |
| 2013/0136655 A1* | 5/2013 | Soberon et al. | 422/186.04 |
| 2013/0147340 A1* | 6/2013 | Holbeche | 313/231.31 |
| 2013/0202766 A1* | 8/2013 | Rubinsky et al. | 422/186.04 |
| 2013/0345620 A1* | 12/2013 | Zemel et al. | 604/24 |
| 2014/0044595 A1* | 2/2014 | Keener | A61L 2/14 422/23 |

FOREIGN PATENT DOCUMENTS

| | | |
|---|---|---|
| JP | 5004079 B2 | 11/2008 |
| WO | PCTUS2012027571 | 3/2012 |
| WO | WO 2012/122045 A2 | 9/2012 |
| WO | WO 2012175066 A1 * | 12/2012 |

OTHER PUBLICATIONS

Machine translation of DE 10 2008 045 507 A1.*

Santhanakrishnan et al., "Flow Control With Plasma Synthetic Jet Actuators", Jan. 19, 2007, pp. 637-651, vol. 40, No. 2007, Publisher: Journal of Physics D: Applied Physics, Published in: US.

PCT/US2013/059759, Applicant: The Board of Regents for Oklahoma State University, filed Sep. 13, 2013, "International Search Report and Written Opinion" dated Dec. 5, 2013.

Ozturk et al., "Parametric Study of Thrust Generation in Plasma Microthrusters", 2008, Publisher: American Institute of Aeronautics and Astronautics, Published in: US.

Bolitho et al., "Thrust Vectoring Flow Control Using Plasma Synthetic Jet Actuators", Jan. 4, 2008, Publisher: American Institute of Aeronautics and Astronautics, Published in: US.

Santhanakrishnan, et al., "On Plasma Synthetic Jet Actuators", "44th AIAA Aerospace Sciences Meeting and Exhibit, Jan. 9-12, 2006, Reno, NV".

* cited by examiner

PLASMA POUCH

FIELD OF THE INVENTION

This disclosure is related to plasma technologies in general and, more particularly, to plasma apparatus for biological decontamination and/or sterilization.

BACKGROUND OF THE INVENTION

Plasma actuators are zero-net mass flux (ZNMF) devices that use atmospheric pressure electrical discharges. These discharges are from a class that includes corona discharges, dielectric barrier discharges (DBDs), glow discharges and arc discharges. Plasma is further known to be a sterilization medium for a number of biological agents through some combination of the mechanisms of heat, ultraviolet radiation, ionization, etc. However, the items to be sterilized must be placed within the plasma itself, possibly damaging the device to be sterilized and limiting the scope and efficacy of the sterilization volume.

What is needed is a system and method for addressing the above, and related, concerns.

SUMMARY OF THE INVENTION

The invention of the present disclosure, in one aspect thereof, comprises a device with a pouch having a pouch wall with an inner side and an outer side, the pouch wall defining an interior of the pouch. The device includes a plurality of electrodes embedded in the pouch wall with at least one electrode partially exposed within the interior of the pouch. The plurality of electrodes generate plasma within the interior of the pouch in response to application of voltage to the plurality of electrodes.

In some embodiments, the pouch wall comprises a flame and shock resistant outer covering on the outer side of the pouch wall. The electrodes may be at least partially embedded in a dielectric medium on the inner side of the pouch wall. A substrate may interpose the outer covering and the dielectric medium. The device may include a power supply that supplies voltage to the electrodes for the generation of plasma.

The pouch may have a sealable opening. In some embodiments, the device includes an outlet hose passing from the inner side to the outer side of the pouch wall for evacuating gases within the pouch. A filter unit may be connected to the outlet hose.

The invention of the present embodiment, in another aspect thereof, comprises a device having a substrate, a dielectric medium on a first side of the substrate, and a plurality of electrodes affixed to the substrate that generate plasma on the first side of the substrate in response to application of an electric voltage. The device includes an outer covering on a second side of the substrate. The substrate, dielectric medium, and outer covering form a flexible wall such that plasma is generated on a first side of a wall and a second side of the wall is protected from plasma exposure.

In some embodiments, the flexible wall is configured as a pouch with an opening. The pouch may be configured to produce plasma on an interior thereof. In other embodiments, the pouch produces plasma on an exterior thereof. An outlet hose may pass from the inside to the outside of the pouch. The device may include a power supply electrically connected to the plurality of electrodes and providing a voltage thereto for the generation of plasma.

The invention of the present disclosure, in another aspect thereof, comprises a method including providing a substrate, providing a dielectric medium on a first side of the substrate, and providing a plurality of electrodes affixed to the substrate. The method includes providing an outer covering on a second side of the substrate. A flexible wall is formed from the substrate, dielectric medium, and outer covering. A pouch is formed using the flexible wall with an open end and having the outer covering on an outside of the pouch. The method may also include providing a voltage to the plurality of electrodes to generate plasma on an interior of the pouch.

In some embodiments, the method includes providing a sealable closure on the open end. An evacuation hose passing from the interior of the pouch to an exterior of the pouch may be provided. The method may include evacuating at least part of the air inside the pouch via the hose, and/or providing a plasma feed gas into the pouch via the hose.

DETAILED DESCRIPTION OF THE PREFERRED EMBODIMENTS

In various embodiments of the present disclosure a plasma actuator is used for biological decontamination. Some embodiments of the present disclosure are based on the one atmosphere uniform glow discharge or single dielectric barrier discharge concept of cold plasma generation.

Figure 1:
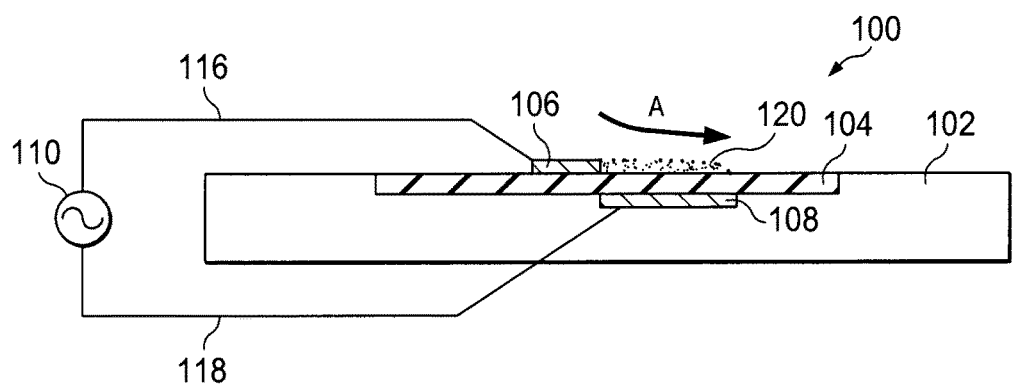
FIG. 1 is a schematic diagram of one embodiment of a plasma generating device according to the present disclosure.

Referring now to FIG. 1, a schematic diagram of one embodiment of a plasma generating device according to the present disclosure is shown. In the embodiment of FIG. 1, the device 100 includes a substrate 102 onto which the various other components described herein may be attached.

As will be explained in greater detail below, the substrate 102 could be a portion of a chamber or enclosure. A suitable substrate 102 would be a non-conductive, impermeable material that is resistant to high temperatures or gas species. Glass, acrylic or phenolic materials are examples of acceptable materials.

Integrated with the substrate 102, or forming a part of the substrate 102, is a dielectric layer 104. The dielectric layer 104 could be formed, by way of example only, from any material with a low dielectric constant such as PTFE or kapton.

An electrode 106 is situated along a top surface of the dielectric layer 104. A second electrode 108 is situated along a lower surface of the dielectric layer 104. It can be seen that the electrodes 106, 108, are at least somewhat offset from one another along a length of the dielectric layer 104. The electrodes 106 and 108 might be made of copper or any other material with suitable conductivity.

The electrode 106 attaches to a voltage source 110 by an electrical lead 116. The electrode 108 attaches to the voltage source 110 by an electrical lead 118. In the present embodiment, the voltage source 110 may include a power supply as well as any necessary transformers or circuit conditioning components to enable generation of plasma by application of sufficient voltage between the electrodes 106, 108 on the surface of the dielectric layer 104. In the present embodiment, a plasma region 120 develops between the first electrode 106 and the second electrode 108. The plasma region 120 also provides a motive force for any adjacent gases in the direction of the arrow "A".

Various duty cycles and voltages may be utilized to generate plasma. In the present embodiment, various voltages, frequencies and duty cycles have been tested and found to be operational. By way of example only, these include voltages in the range of 5 to 50 kV at frequencies of 1,000 to 10,000 Hz at a 10% to 100% duty cycle at modulated frequencies of 1, 2, 5, 10, 100, 500 and 5000 Hz. It will be appreciated that various flow rates and associated decontamination characteristics can be generated by adjusting the duty cycle voltage and frequency of the applied voltage. In application, the limit is most likely to be the durability of the materials used to construct the device 100 and the available power supply. For example, if operating from commercial power, higher voltages may be available than if operating from battery power.

Figure 2:
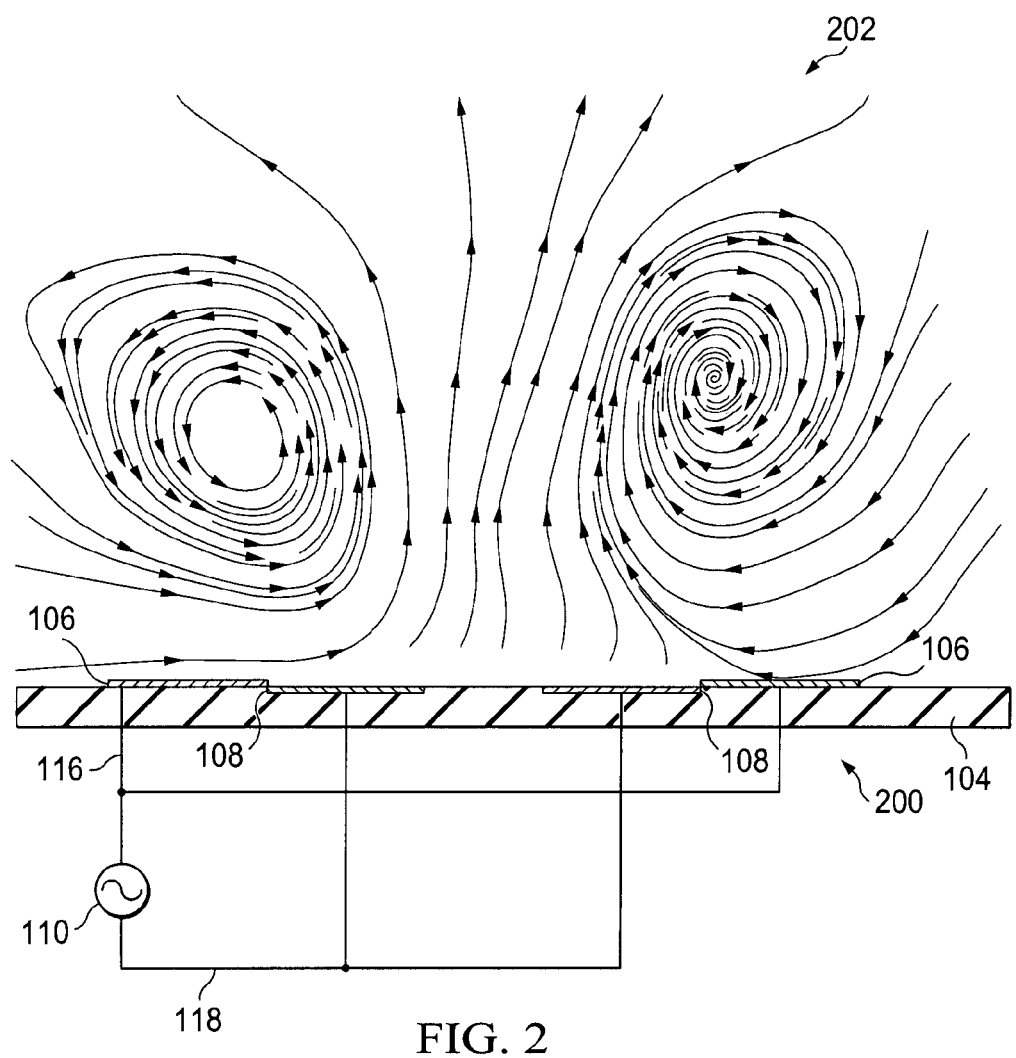
FIG. 2 is a schematic diagram of another plasma generating device according to the present disclosure.

Referring now to FIG. 2, a schematic diagram of another plasma generating device according to the present disclosure is shown. The device 200 is similar in construction and operation to the device 100 of FIG. 1. In the present device, two upper electrodes 106 are attached opposite a dielectric layer 104, and are offset from a pair of lower electrodes 108. Electrical lead 116 attaches the upper electrodes 106 to the voltage source 110 and a lower electrical lead 118 attaches the lower electrodes 108 to the voltage source 110.

In the present embodiment, it will be appreciated that, due to the configuration of the electrodes 106 relative to the electrodes 108, flow regions that are pointed in substantially opposite directions will be achieved. Thus, each electrode pair 106, 108, will generate plasma as well as a motive force pointed inward according to FIG. 2. This will cause a swirling effect of any adjacent gases as illustrated by the exemplary flow lines 202.

In FIG. 2, both of the upper electrodes 106 are shown attached to a common voltage line 116. Similarly, the lower electrodes 108 are shown attached to a common voltage line 118. Thus, in operation, in this embodiment the upper electrodes 106 will always be at the same voltage potential while the lower electrodes 108 will likewise share a voltage potential. However, it is understood that other configurations are possible. For example, both of the upper electrodes 106 need not necessarily be operated at the same voltage level. Similarly, the lower electrodes 108 could be attached to different voltage levels. In this manner the device 200 may be operated in a pulsing fashion where the gas flow is first in one direction, and then in another. It will be appreciated that both of the aforedescribed exemplary operating methods will result in a thorough mixing of gases next to and around the device 200. Thus, over time the adjacent gases will be exposed to the plasma generated by the device and the air thereby decontaminated from biological agents.

Figure 3:
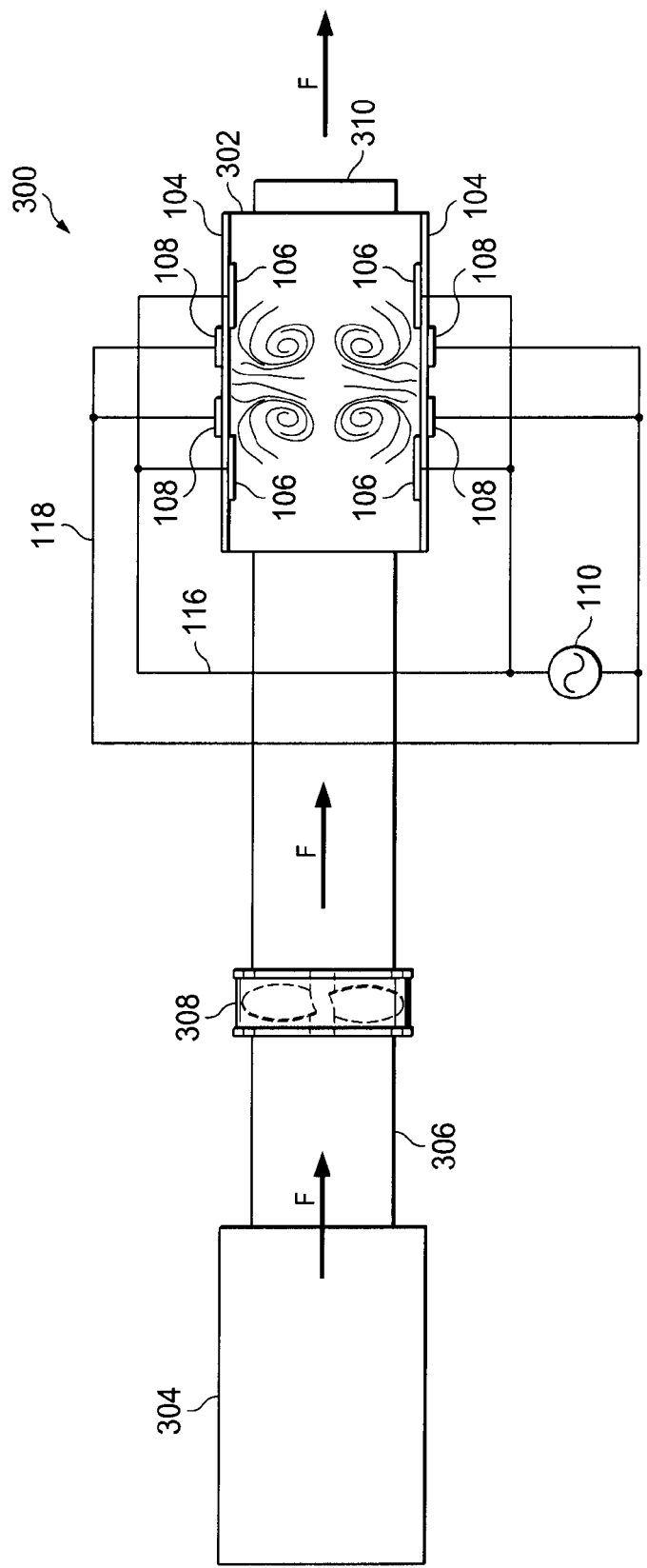
FIG. 3 is a schematic diagram of a plasma decontamination system according to the present disclosure.

Referring now to FIG. 3, a schematic diagram of plasma decontamination system according to the present disclosure is shown. The plasma decontamination system 300 comprises a plasma decontamination chamber 302. This chamber 302 may have a plurality of inner electrodes 106 separated from a plurality of outer electrodes 108 by a dielectric layer 104. The dielectric layer 104 may be enclosed by a substrate (not shown).

The inner electrodes 106 may attach to a voltage source 110 by a lead 116. The outer electrodes 108 may attach to the voltage source 110 by a lead 118. The plasma decontamination system 300 operates in a manner similar to those previously described in that voltages will be applied to the plurality of inner electrodes 106 and outer electrodes 108 generating plasma inside the plasma decontamination chamber 302. The motive forces provided by the plasma generation will serve to mix and swirl gas within the plasma decontamination chamber 302 such that the gases inside of the chamber 302 may be substantially completely decontaminated from biological agents.

In some embodiments, the motive force for drawing contaminated air into the plasma decontamination chamber 302, and expelling decontaminated air, will be entirely due to the location and configuration of the plasma generating electrodes 106, 108 in and on the plasma decontamination chamber 302. However, in other embodiments, a separate flow control system may be utilized that provides for selective introduction of contaminated gases into the decontamination chamber 302 from a contamination source 304. The contamination source 304 could be naturally or otherwise occurring bacteria or viruses, medical waste, sewage or any number of sources which generate air containing bio-contaminants. In the present embodiment, the gases flow generally from the contamination source 304 in the direction of the arrows "F".

A conduit 306 is provided between the plasma decontamination chamber 302 and the contamination source 304. A fan 308 may be provided that produces vacuum toward the contamination source 304, and positive pressure toward the plasma decontamination chamber 302. The fan 308 or other flow driving device may operate in an open-loop configuration or may be selectively activated such that air within the decontamination chamber 302 has sufficient time for exposure to plasma to achieve a satisfactory level of decontamination. An exit conduit 310 may be provided for moving the decontaminated gas away from the decontamination chamber 302. In some embodiments, the exit conduit 310 will merely function as a selectively closeable valve to prevent air from escaping the decontamination chamber 302 until sufficiently and effectively decontaminated.

Figure 4:
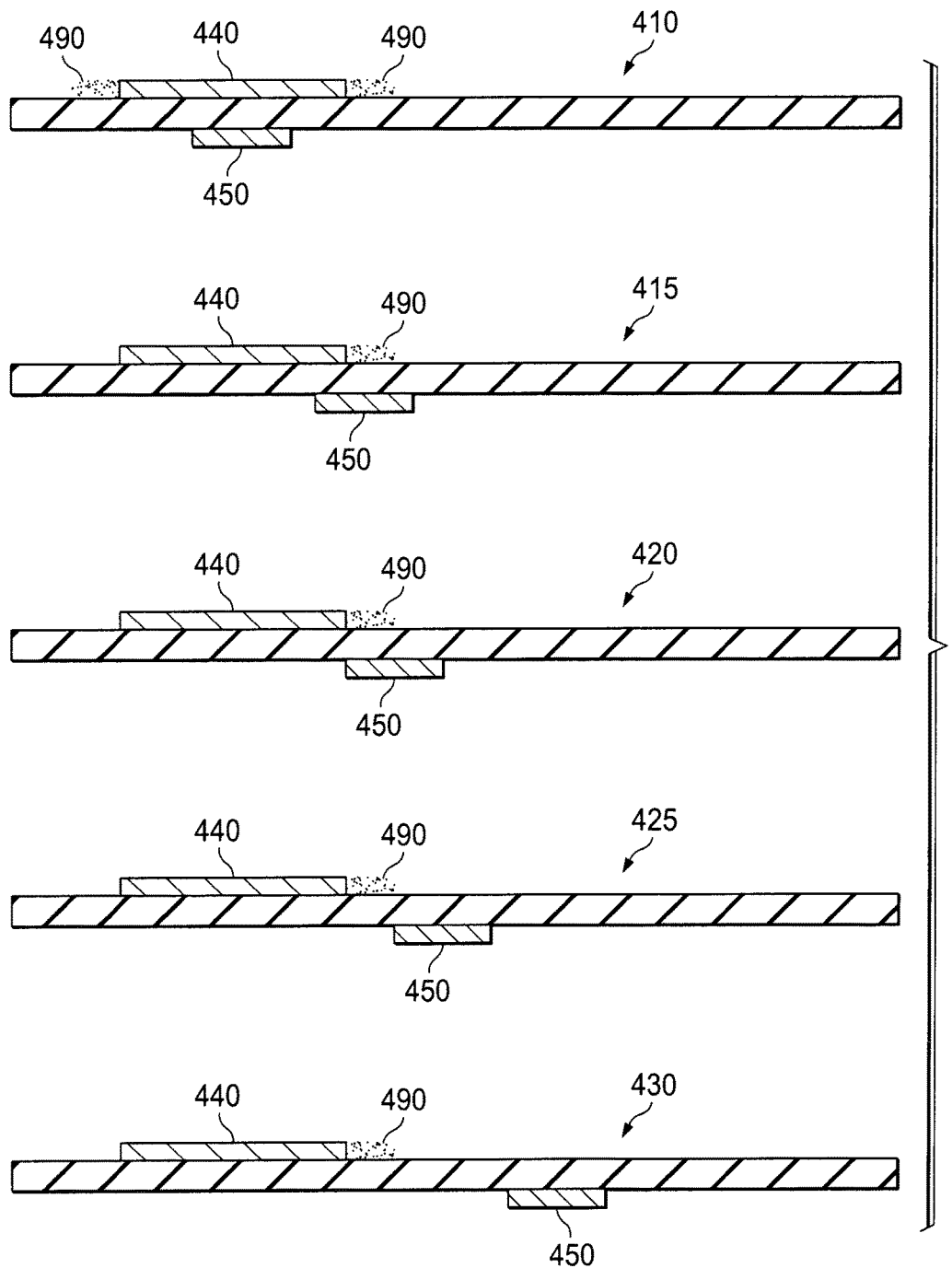
FIG. 4 contains some example relative positions of upper and lower conductors that would be suitable for use with various embodiments the present disclosure.

FIGS. 4 through 11 illustrate additional embodiments of the present disclosure. In FIG. 4, configuration 410 is an embodiment that operates to generate a plasma stream 490 on both sides of the upper conductor 440 at its periphery.

However, some embodiments tend to produce better results when the upper 440 and lower 450 conductors at least partially overlap, tends to produce better results (e.g., 410 and 415). Further, and continuing with the examples of FIG. 4, configurations such as 420 to 430 tend to show generally decreasing performance as compared with configuration 415. Obviously, if the conductors are spaced sufficiently far apart the plasma generated will be negligible or zero.

Figure 5:
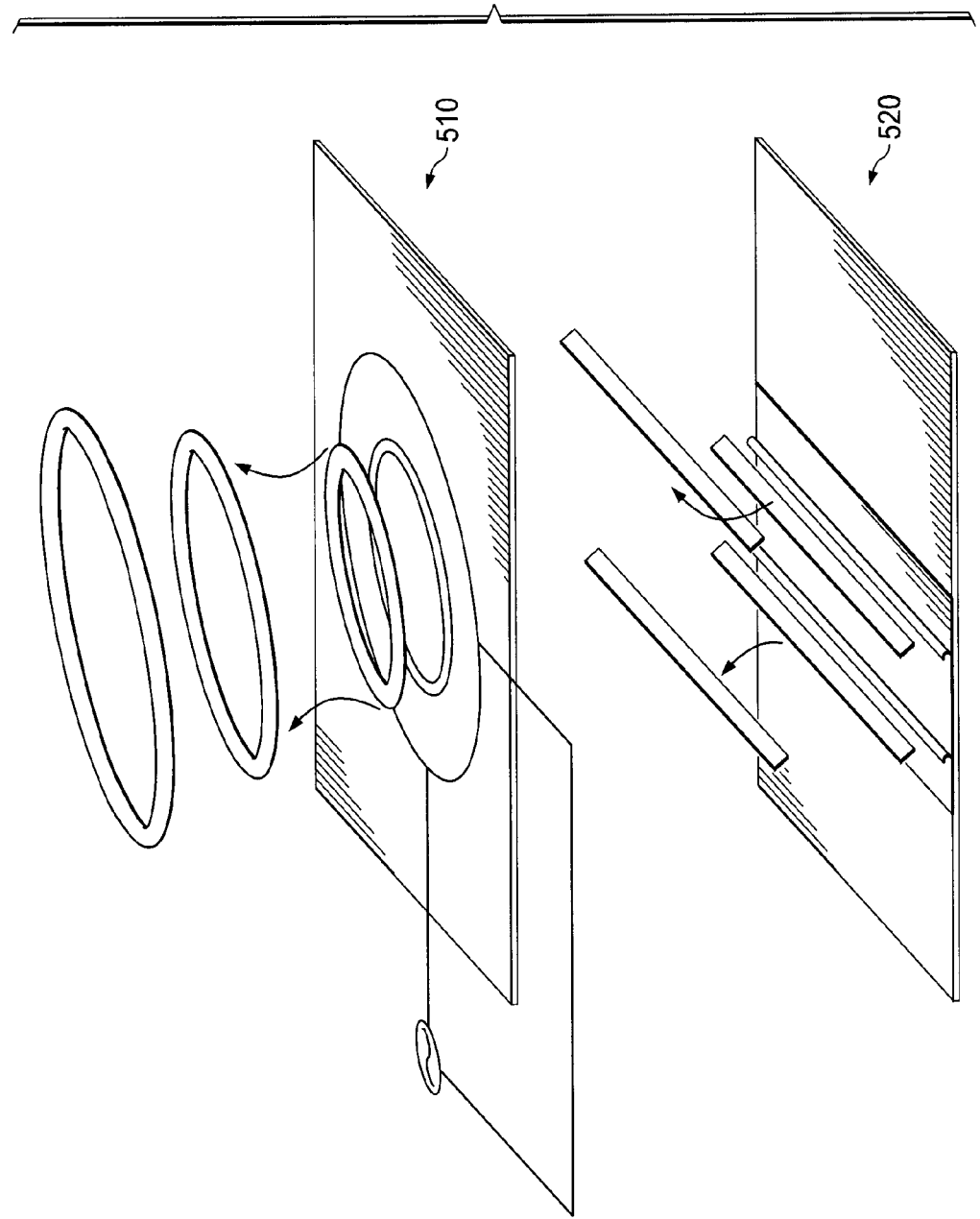
FIG. 5 contains schematic illustrations of linear and annular examples of the present disclosure.

FIG. 5 contains a schematic illustration of linear 520 and annular 510 embodiments. As can be seen, in the embodiments of this figure the motive force associated with the plasma stream is in an outward (upward by reference to this figure) direction, i.e., a "blow" embodiment. That being said, if the electrical leads are reversed, a downward/inward (i.e., a "suck") embodiment can be created.

Figure 6:
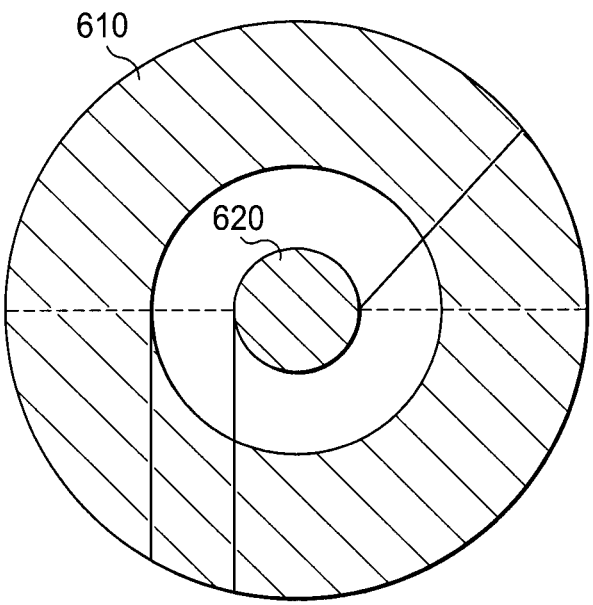
FIG. 6 contains additional details of an annual embodiment.
Figure 7:
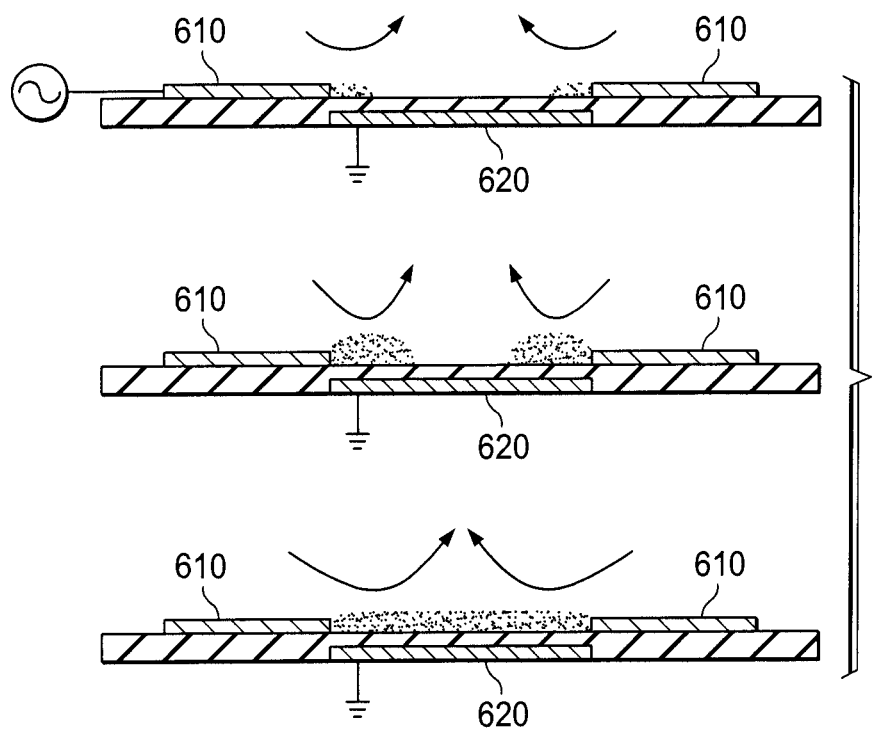
FIG. 7 illustrates relative motive force for some different configurations of the embodiment of FIG. 6.

FIGS. 6 and 7 contain additional details of an annual embodiment. In the configuration of FIG. 6, note that the amount of plasma generated and the corresponding motive force can be varied by increasing the voltage differential that is supplied to the electrodes 610 and 620 as is illustrated generally in FIG. 7.

Figure 8:
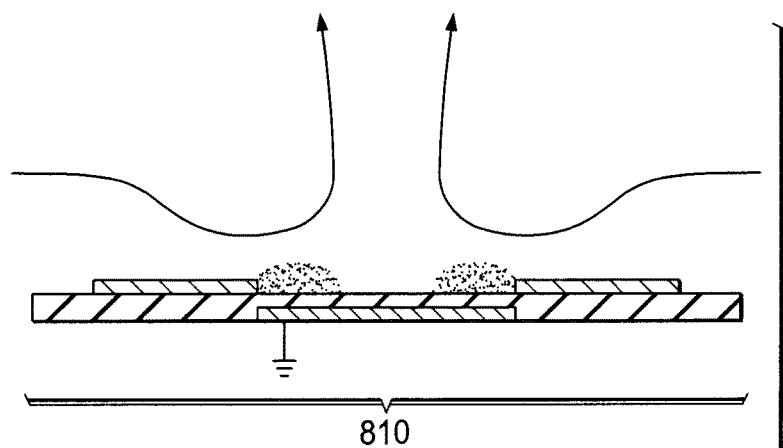
FIG. 8 contains schematic illustrations of asymmetrical motive force that will typically be produced by the embodiment of FIG. 6.
Figure 8:
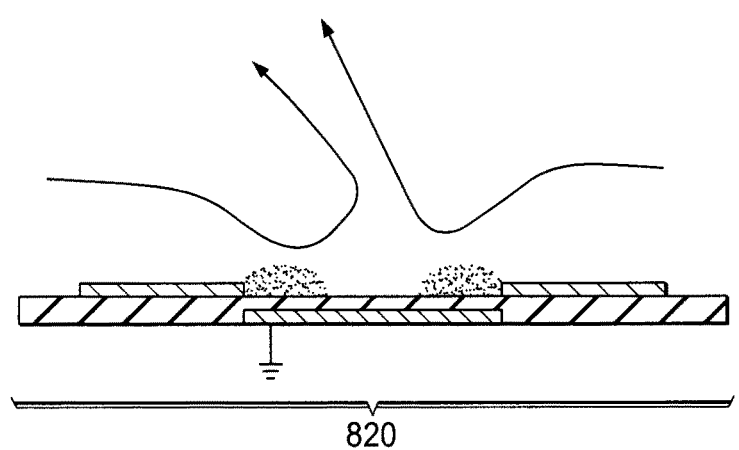

FIG. 8 is a schematic cross-sectional illustration of the embodiment of FIG. 7 that shows that, although the motive force is generally directed orthogonally away from (or toward) the dielectric material, in some configurations and at some points along the embodiment of FIG. 7 that the force may take a path that is non-orthogonal to the dielectric material.

Figure 9:
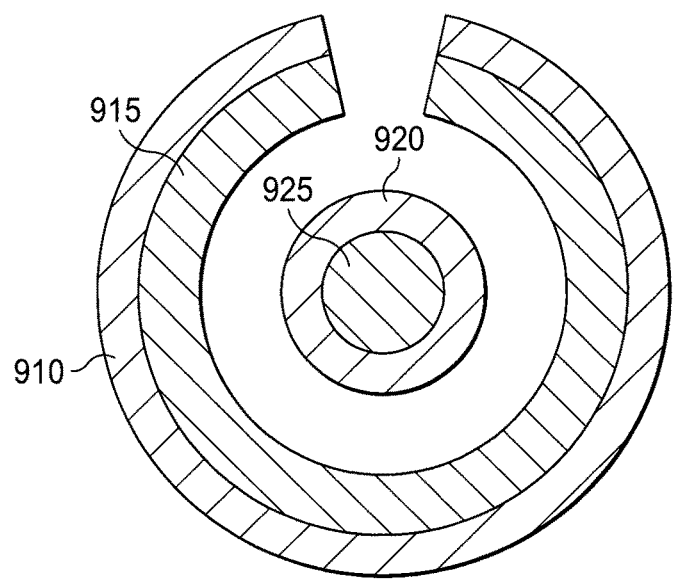
FIG. 9 contains still another embodiment of the present disclosure wherein multiple annular electrodes are used.
Figure 10:
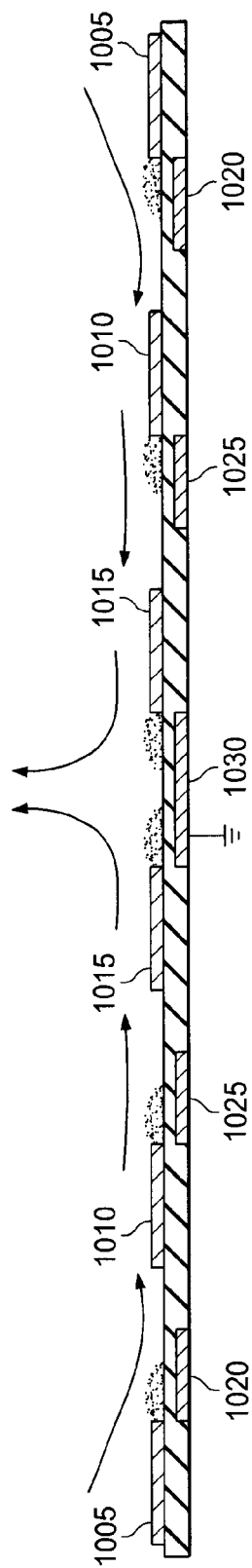
FIG. 10 illustrates a cross sectional view of another annular embodiment of the present disclosure.

FIGS. 9 and 10 are schematic illustrations of still other arrangements that are generally annular. FIG. 9 contains an illustration of an annular embodiment that includes two upper electrodes 910 and 920 and two lower electrodes 915 and 925. Note that the electrodes 910 and 920 might be electrically isolated from each other or not. The same might also be said with respect to electrodes and 915 and 925.

FIG. 10 contains a cross-sectional view still another annular embodiment, with upper electrodes 1005, 1010, and 1015, and lower electrodes 1020, 1025, and 1030. Note that in some embodiments (e.g., FIGS. 7, 8, and 10) one or more electrodes, e.g., the lower electrode in these figures, is embedded in the dielectric.

Figure 11:
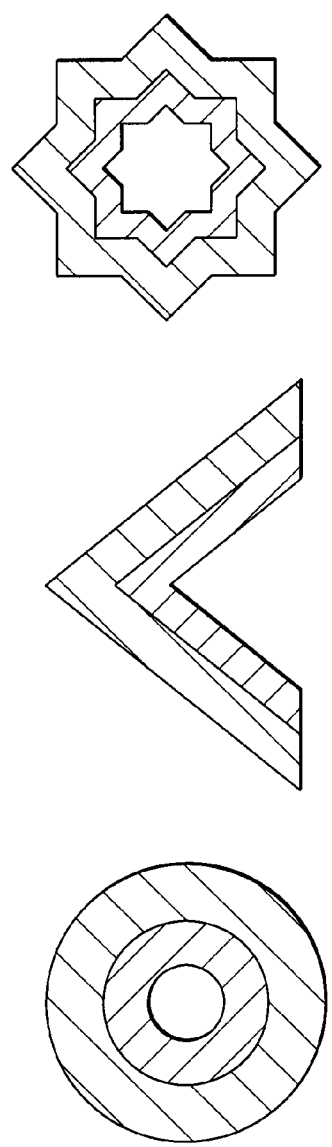
FIG. 11 contains schematic illustrations of some other configurations of the present disclosure.

FIG. 11 contains some further embodiments, e.g., annular, chevron, and hybrid. Those of ordinary skill in the art will readily be able to devise other shapes and arrangements that generate plasma according to the instant disclosure.

Note that, although in some embodiments the dielectric is a generally rectangular single planar surface, in other embodiments it might be round, polygonal, etc. Additionally, in still other embodiments the dielectric might be separated into two or more pieces that are interconnected by conductive material. In such an instance, the electrodes of the instant disclosure might be placed on the same or different pieces of the dielectric. The dielectric and/or associated electrodes might also be non-planar depending on the requirements of a particular application. Thus, for purposes of the instant disclosure it should be understood that the term "dielectric" is applicable to materials that are any shape, that are planar or not, and that might be divided into multiple pieces that are joined by conductive materials.

Further note that for purposes of the instant disclosure, the term "length" should be broadly construed to be any linear dimension of an object. Thus, by way of example, circular dielectrics have an associated length (e.g., a diameter). The width of an object could correspond to a length, as could a diagonal or any other measurement of the dielectric. The shape of the instant electrodes and associated dielectric are arbitrary and might be any suitable shape.

Still further, note that the voltages applied to the top and bottom electrodes will be different. It is important that the voltage differential between the electrodes be sufficient for the generation of plasma, e.g., about 5 to 50 kV as was discussed previously. The positive electrode can either be on the top or the bottom of the dielectric and the orientation might be varied depending on the direction it is desired to have the plasma stream move.

Finally it should be noted that remembered that the tem "offset" as used herein should be broadly construed to include cases where there is no overlap between the electrodes (e.g., configurations 425 and 430) as well as cases where there is substantial overlap (e.g., configuration 410). What is important is that the edges of the upper and lower electrodes not be completely coincident, e.g., one electrode or the other should have a free edge (or part of an edge) that does exactly overlay the corresponding electrode on the opposite surface.

Figure 12:
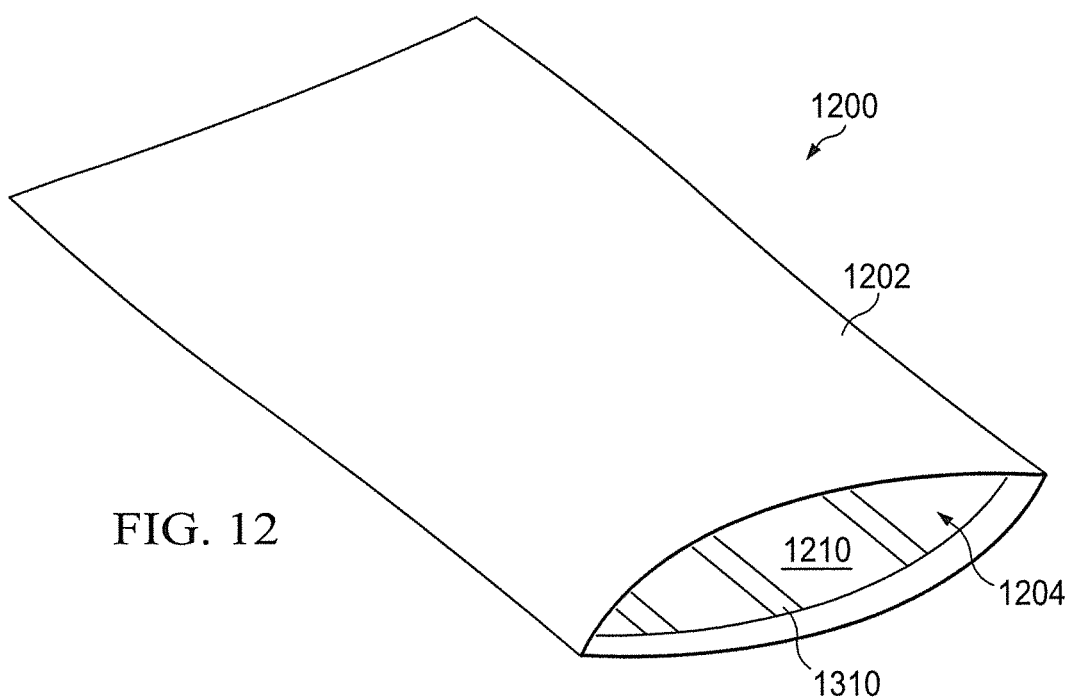
FIG. 12 is a perspective view of a plasma pouch decontamination device according to the present disclosure.

Referring now to FIG. 12 a perspective view of one embodiment of a plasma pouch decontamination device according to the present disclosure is shown. The pouch 1200 represents on application of the plasma generation devices disclosed herein. The pouch 1200 may be constructed in various sizes to allow sterilization of differently sized articles. For example, the pouch 1200 can have multiple compartments like a piano file, and/or it can be constructed to substantially conform to the geometric outline of the object device to be disinfected or sterilized. In other examples, the pouch 1200 can be produced as a mitten. A mitten or glove configuration may be constructed "inside out" such that plasma is generated on the exterior (e.g., for hand held decontamination of instruments). Some embodiments will provide a sheath-like sterilization pouch, which can be used to decontaminate the surfaces of long, serpentine bodies such as those of catheters and other devices.

The pouch 1200 may comprise a body portion 1202 that may be folded around on itself to create an interior 1210 of the pouch 1200. The body portion 1202 may be sealed at all but one edge that forms an opening 1204. The opening 1204 allows for insertion and removal of articles to be sterilized. Within the interior 1210 of the pouch 1200 a plurality of plasma-generating electrodes 1310 can be seen. These electrodes 1310 may cover a portion, or substantially all, of the interior 1210 of the pouch 1200.

Figure 13:
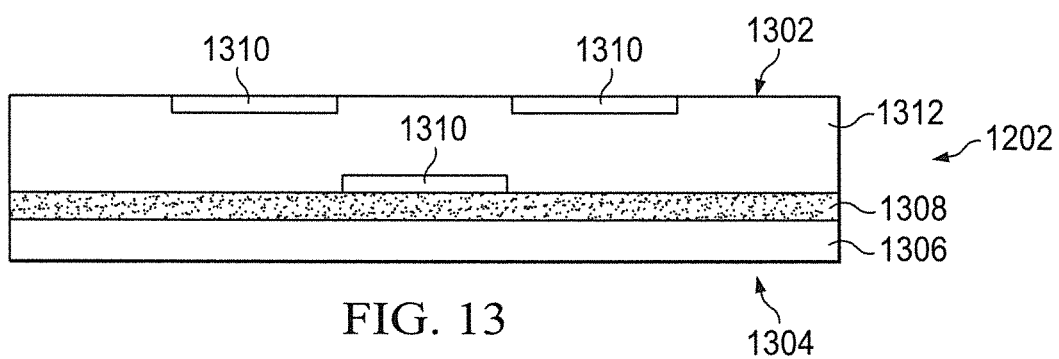
FIG. 13 is an end cutaway view of the plasma pouch of FIG. 12.

Referring now to FIG. 13, an end cutaway view of a portion of the plasma pouch 1200 is shown. The body portion 1202 can be seen to comprise an inner side 1302 corresponding to the interior 1210 of the pouch 1200, and an outer side 1304 corresponding to an exterior of the pouch 1200. The outer side 1304 may be covered by a flame and shock retardant material 1306 comprising an outer layer. This material 1306 may be similar to, or the same as, material utilized in fire resistant blankets. This may help to prevent any damage due to electricity or plasma to any objects or supporting surfaces outside the pouch 1200. The material 1306 may also protect against shorting or burnout of interior dielectric material.

A substrate 1308 may be provided under, or next to, the outer layer material 1306. The substrate 1308 may comprise materials such as Teflon® or polyethylene film. The substrate 1308 seals at least some of a plurality of electrodes 1310 against contact with air, and thus prevents generation of plasma on sealed surfaces. The pattern of the electrodes 1310 in the pouch can also implement various geometries (e.g., as discussed above). Thus, flow within the pouch 1200 can be controlled based on electrode geometry. In some embodiments, metallic tape or etched powdered electrodes may be used due to their flexibility.

The electrodes 1310 are restrained in a dielectric medium 1312. In some embodiments, the medium 1312 is a flexible film. This provides flexibility for the pouch 1200 and increases the number of geometries of electrodes that can be generated. The medium 1312 may range from less than 0.005 inches to about 0.010 inches in thickness. The thickness of the entire layer 1202 is only a few millimeters thick in some embodiments.

Figure 14:
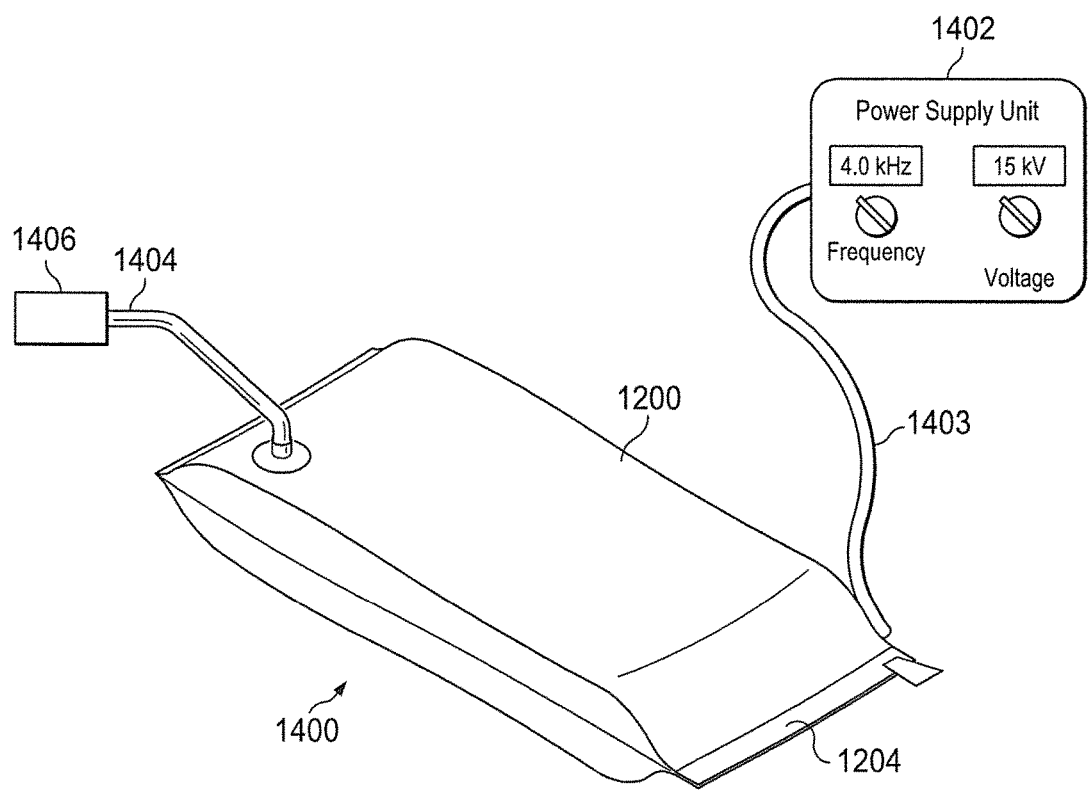
FIG. 14 is a perspective view of a system employing the plasma pouch of FIG. 12 for decontamination purposes.

Referring now to FIG. 14, a perspective view of a system 1400 employing the plasma pouch 1200 of FIG. 12 for decontamination purposes. The system 1400 employs a power supply 1402 that includes a transformer and a wall supply plugin. The power supply may provide a fixed voltage and frequency. In other embodiment, the power supply may have a variable voltage. In some cases the range will be from about 5 kV to 20 kV and may have a frequency between 600-5000 Hz. Switches and other controls may be provided for operation of the power supply 1402.

The power supply 1402 is electrically connected to the plasma pouch 1200 and to the internal electrodes (e.g., 1310 of FIG. 13). It is understood that a plurality of electrical leads may be combined into a single cord 1403 that enters the pouch 1200 (or pouch wall 1202) for connection to the electrodes 1310.

In operation, it may be useful to evacuate a certain amount of air from the pouch 1200 once the object to be decontaminated has been placed inside. This may result in a drop in the internal pressure of the pouch 1200 and/or a tendency for the pouch walls 1202 to adhere to the exterior of the contaminated object's surface. This helps reduce the distance between the plasma and the contaminated surface, allowing short lived species, such as Reactive Oxygen Species (ROS), to reach the surface of the object to be disinfected or sterilized.

The opening 1204 of the pouch 1200 may be sealable to prevent any gases and/or plasma generated species from escaping. This results in a complete inactivation mechanism. It also prevents a number of unwanted volatile gases and hazardous contaminants from escaping and potentially damaging nearby equipment or becoming a hazard to personnel.

Internally within the pouch 1200, vortices are generated due to the body forces in surface discharges. This results in complete mixing of all the generated species to produce a very lethal "antimicrobial soup". The by-products generated in the process (e.g., ozone), may be ventilated out through a filter unit 1406 attached to outlet hose 1404. Activated carbon is one filter media that may be used. Other reducing agent embedded filters may also reduce byproducts such as ozone to a less harmful form. In a similar fashion number of other materials can be used to adsorb other by-products such as NOx.

The pouch 1200 and/or the entire system 1400 may also be used for the purpose of cleaning surfaces through etching of both organic and inorganic molecules. Gaseous mixtures such as $O_2$ and $CF_4$ have a high etching ability when used as feed gas for plasma instead of air. In one embodiment, they are injected into the pouch 1200 via outlet hose 1404. Valving (not shown) may be utilized to allow the same hose 1404 to be used for evacuation of gases and by product and the introduction of gases into the pouch 1200.

The pouch 1200 may have a number of sensors and actuators to boost its performance. For example, the pouch 1200 may contain proximity sensors and/or electric relays to shut down the discharge if a short or burn-out is detected. Ozone and other particulate concentration sensors may be used to detect leaks in pouch 1200.

In some embodiments, the pouch 1200 may incorporate the use of dyes or other reactive chemical agents. For example, an azo dye can be used to determine whether a required sterility level has been achieved. Based on laboratory results, the time frame utilized for sterilization may be adjusted.

It is understood that the pouch 1200 and/or the system 1300 can be replicated or expanded. For example, for large facilities, multiple pouch arrays can be established to run in tandem for large number of articles to be sterilized. It is also understood that multiple pouches 1200 may be operated by a single power supply 1402.

REFERENCES

[1] Y. Takeuchi, and T. Itoh, "Removal of ozone from air by activated carbon treatment", Sep. Technol., vol. 3, pp. 168-175, July 1993.

[2] S. Lerouge, M. R. Wertheimer, and L. H. Yahia, "Plasma Sterilization: A Review of Parameters, Mechanisms, and Limitations", Plasmas and Polymers, Vol. 6, No. 3, pp. 175-187, Sep. 2001.

[3] M. Mikumo, K. Kazama, "Plasma Sterilization Indicator", U.S. Patent 2011/0009535 A1, issued Jan. 13, 2011.

* * *

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. A device comprising:
   a pouch having a flexible pouch wall with an inner side and an outer side, the pouch wall defining an interior of the pouch with a sealable opening and having a flame and shock resistant outer covering adjacent to a substrate, which is adjacent to an inner dielectric medium; and
   a plurality of inner electrodes embedded in the pouch wall with at least one of said plurality of inner electrodes partially exposed from the dielectric medium within the interior of the pouch, each of said plurality of inner electrodes being positionable to be directly connected with a power supply;
   two or more outer electrodes sealed from exposure to air between the dielectric medium and the substrate,
   each of said two or more outer electrodes being positionable to be simultaneously powered using said power supply,
   each of said outer electrodes having at least one inner electrode proximate thereto,
   wherein each of said outer electrodes only partially overlaps at least one of said at least one proximate inner electrode,
   wherein the plurality of inner electrodes generate plasma within the interior of the pouch in response to application of a voltage to both of the plurality of inner electrodes and the plurality of outer electrodes;
   wherein the plurality of inner and outer electrodes are sufficient in number and provided with sufficient voltage so as to provide plasma to substantially an entire surface of a solid object within the pouch to decontaminate the object in a single operation.

2. The device of claim 1, wherein said power supply is directly connected to said plurality of electrode pairs.

3. The device of claim 1, further comprising an outlet hose passing from the inner side to the outer side of the pouch wall for evacuating gases within the pouch.

4. The device of claim 3, further comprising a filter unit connected to the outlet hose.

5. A device comprising:
a substrate;
a dielectric medium on a first side of the substrate;
a plurality of electrode pairs adjacent to the dielectric medium that generate plasma on a side of the dielectric medium opposite the substrate in response to application of an electric voltage; and
an outer covering on a second side of the substrate;
wherein one electrode of each pair of the plurality of electrode pairs is at least partially exposed on the side of the electric medium opposite the substrate, and one electrode of each pair of the plurality of electrode pairs is sealed from exposure to air between the dielectric medium and the substrate;
wherein the partially exposed electrode of each electrode pair and the sealed electrode of each electrode pair are positionable to be placed simultaneously into direct electrical contact with the applied voltage;
wherein the substrate, dielectric medium, and outer covering form a flexible pouch having an inside and an outside such that plasma is generated on the inside of the pouch and the outside of the pouch is protected from plasma exposure;
wherein the partially exposed electrode of each electrode pair and the sealed electrode of each electrode pair are positioned so as to only partially overlap each other so that a motive force urges the plasma generated by each of said electrode pair toward the inside of said pouch when said electrode pair is placed into direct electrical contact with the applied voltage;
wherein the plurality of electrode pairs are sufficient in number and provided with sufficient voltage so as to provide plasma decontamination of substantially an entire surface of a solid object within the pouch in a single operation without a separate mixing process.

6. The device of claim 5, wherein the pouch provides a sealable opening.

7. The device of claim 6, further comprising an outlet hose passing from the inside to the outside of the pouch.

8. The device of claim 5, further comprising a power supply electrically connected to the plurality of electrode pairs and providing a voltage thereto for the generation of plasma.

9. A method comprising:
providing a substrate;
providing a dielectric medium on a first side of the substrate;
providing an outer covering on a second side of the substrate;
providing a plurality of electrode pairs affixed to the dielectric medium with one electrode of each pair exposed on a side of the dielectric medium opposite the substrate and one electrode of each pair sealed from exposure to air by the dielectric medium and the substrate;
forming a flexible wall from the substrate, dielectric medium, and outer covering;
forming a pouch with a sealable open end and having the outer covering on an outside of the pouch using the flexible wall;
inserting a solid object into the pouch and sealing the open end; and
providing a voltage simultaneously to each of the plurality of electrode pairs to generate plasma on an interior of the pouch sufficient to provide plasma decontamination of substantially the entire surface of the solid object in a single operation without a separate mixing or stirring operation.

10. The method of claim 9, further comprising providing an evacuation hose passing from the interior of the pouch to an exterior of the pouch.

11. The method of claim 10, further comprising evacuating at least part of the air inside the pouch via the hose.

12. The method of claim 11, further comprising providing a plasma feed gas into the pouch via the hose.

* * * * *